United States Patent
Tratt et al.

(10) Patent No.: US 7,422,894 B2
(45) Date of Patent: Sep. 9, 2008

(54) APPARATUS FOR USE IN VERMICULTURE (75) Inventors: Simon James Tratt, Dubbo (AU); Graham Shaun Ankers, Manly (AU)

(73) Assignee: Vermitech Limited, Darlinghurst (AU)

( * ) Notice: Subject to any disclaimer, the term of this patent is extended or adjusted under 35 U.S.C. 154(b) by 365 days.

(21) Appl. No.: 10/531,241

(22) PCT Filed: Oct. 16, 2003

(86) PCT No.: PCT/AU03/01370

§ 371 (c)(1), (2), (4) Date: Jun. 21, 2005

(87) PCT Pub. No.: WO2004/035509

PCT Pub. Date: Apr. 29, 2004

(65) Prior Publication Data

US 2006/0172410 A1    Aug. 3, 2006

(30) Foreign Application Priority Data

Oct. 17, 2002    (AU)    ............................ 2002952147

(51) Int. Cl.
| | |
|---|---|
| C12M 1/02 | (2006.01) |
| C12M 1/00 | (2006.01) |
| B65G 1/00 | (2006.01) |
| B65G 23/00 | (2006.01) |
| B65G 25/00 | (2006.01) |
| B65G 25/02 | (2006.01) |
| B65G 25/04 | (2006.01) |
| B65G 27/00 | (2006.01) |

(52) U.S. Cl. ............... 435/290.3; 435/290.1; 435/290.2; 435/290.4; 198/347.3; 198/832; 198/614; 198/621.1; 198/750.1; 198/754

(58) Field of Classification Search ............... 435/290.3, 435/290.1, 290.2, 290.4; 198/347.3, 832, 198/614, 621.1, 750.1, 754
See application file for complete search history.

(56) References Cited

U.S. PATENT DOCUMENTS 3,533,660 A * 10/1970 Russell ...................... 299/18

(Continued)

FOREIGN PATENT DOCUMENTS

AU    1998 94187    6/1999

(Continued)

*Primary Examiner*—Walter D. Griffin
*Assistant Examiner*—Lydia Edwards
(74) *Attorney, Agent, or Firm*—Steptoe & Johnson LLP (57) ABSTRACT

Apparatus for use in a vermiculture plant, the apparatus including a treatment receptacle having a treatment Apparatus for use in a vermiculture plant which includes a treatment receptacle having a treatment chamber therein and a base upon which material within the treatment chamber is disposed. The receptacle is arranged so that when in use there is a space below the base. The apparatus further includes a harvester operable to extract material from the treatment chamber through the base and a collecting assembly including a flexible belt operatively connected to a rotatable drum so that it can be wound onto or drawn from the rotatable member. The belt is arranged so that it can adopt a collecting position when at least partially unwound from the rotatable member wherein it is positioned below the treatment chamber and harvester so that harvested material can be collected upon it and is operable so that when wound onto the rotatable member material thereon can be transferred to a discharge zone.

14 Claims, 13 Drawing Sheets

U.S. PATENT DOCUMENTS

| | | | | |
|---|---|---|---|---|
| 4,310,414 A | * | 1/1982 | Lux | 210/238 |
| 5,431,289 A | * | 7/1995 | Hoffman | 209/638 |
| 5,527,373 A | | 6/1996 | Chareyre | 71/9 |

FOREIGN PATENT DOCUMENTS

| | | |
|---|---|---|
| EP | 196887 | 10/1986 |
| EP | 887328 | 12/1998 |
| WO | WO 99/51545 | 10/1999 |

* cited by examiner

APPARATUS FOR USE IN VERMICULTURE

The present application is based on International Application PCT/AU2003/001370, filed Oct. 16, 2003, which application is incorporated herein by reference in its entirety.

This invention relates to apparatus for use in vermiculture processes; that is processes whereby organic waste material is treated using worm species.

In applicant's Intentional Patent Specification No. WO 99/51545 (CT/AU99/00238) there is described apparatus for use in vermiculture processes. The contents of the aforementioned patent specification is incorporated into the present specification by way of cross reference.

In the aforementioned specification there is described a treatment apparatus which includes a main body having a treatment chamber therein which includes a base which when the apparatus is in a harvesting mode is arranged with a space therebelow. The base includes a plurality of generally parallel spaced apart support elements, the support elements being spaced apart at a distance sufficient to support the material within the chamber during the treatment process and enable extraction of the treated material through the spaces between the support elements during a harvesting process.

According to one aspect of the present invention there is provided apparatus for use in a vermiculture plant, the apparatus including a treatment receptacle having a treatment chamber therein and a base upon which material within the treatment chamber is disposed, the receptacle being arranged so that when in use there is a space below the base, a harvester operable to extract material from the treatment chamber through the base and a collecting assembly including a flexible belt operatively connected to a rotatable member so that it can be wound onto or drawn from the rotatable member, said belt being arranged so that it can adopt a collecting position when at least partially unwound from the rotatable member wherein it is positioned below the treatment chamber and harvester so that harvested material can be collected upon it, said belt being operable so that when the belt is wound onto the rotatable member material thereon can be transferred to a discharge zone.

The rotatable member may be in the form of a rotatable drum arranged so that the belt can be wound around the drum and retracted from underneath the treatment chamber. Preferably, the discharge zone is disposed adjacent the drum so that as the belt is wound onto the drum material is discharged from the belt. The drum may be either manually operable to powered by a motor or the like.

The collecting assembly may further include a support tray upon which the belt rests when in the collecting position. The support tray may include side walls between which the belt is disposed. Preferably, the belt is porous. Material collected may be transferred to a drying chamber after which it may be transferred to a screening device. The finally treated material may be transferred to storage or dispatch bunkers.

The harvester may include a main frame operatively mounted for movement relative to the main body of the treatment apparatus in a position below the base thereof, the harvester further including tool carried by the frame for extracting material from the treatment chamber. Preferably, the harvester body is suspended from rails disposed adjacent the base of the treatment apparatus or supported on rails spaced from the main body of the treatment apparatus, and includes drive means for causing movement of the main frame along the rails. Preferably, the belt of the collecting assembly is retractable generally in the same direction of movement of the harvester.

The apparatus may further include a feed system, the feed system including a material distributor assembly for distributing the material into the treatment chamber, the distributor assembly including a distributor conveyor which is adapted to be wound onto or from a rotatable member, the assembly further including a carriage which is adapted to traverse over the top of the treatment chamber, the carriage including an idler roller thereon over which the distributor conveyor passes with its free end being anchored to a fixed structure.

The apparatus may include a plurality of treatment receptacles disposed one above the other in a tiered configuration. In one form each treatment receptacle has associated therewith one said harvester and one said collecting assembly.

In another embodiment one harvester is adapted to be moved into a harvesting position on each treatment receptacle and said flexible belt of the collecting assembly is adapted to be positioned in a collecting position for use with each treatment receptacle. To this end a lifting mechanism may be provided for transferring the harvester and the flexible belt of the collecting assembly between the treatment receptacles. In one form a single rotatable member can be used for moving said harvester and said flexible belt of said collecting assembly. In another arrangement each treatment receptacle has associated therewith a collection belt In this arrangement a single harvester is provided with a plurality of belts each belt associated with a respective treatment receptacle. If desired more than one harvester could be provided but not necessarily one for each receptacle.

According to another aspect of the present invention there is provided apparatus for use in vermiculture processes, the apparatus including a pretreatment system for pretreating the waste material, a feed system and a treatment system, the feed system being adapted to feed the waste material to the treatment system. The apparatus may further include a harvesting and collecting system.

As discussed earlier the treatment system may be of the type described in the aforementioned Intentional patent specification either in its broad or more specific forms.

The pretreatment system may include a mixing vessel to which unprocessed waste material is delivered from storage bunkers. The mixing vessel may in one form include a mixer which may include rotating paddles driven by a motor which mixes the material within the vessel.

According to yet another aspect of the present invention there is provided a feed system for use in apparatus described above, the feed system including a material distributor assembly for distributing the material into the treatment chamber. The distributor assembly may include a distributor conveyor which is adapted to be wound onto or from a conveyor drum. The assembly may further include a carriage which is adapted to traverse over the top of the treatment chamber. The carriage may include an idler roller thereon over which the distributor conveyor passes with its free end being anchored to a fixed structure. Thus as the carriage moves over the treatment chamber the conveyor is drawn from the drum and passes around the idler drum so that material on the conveyor is evenly distributed into the treatment chamber. The carriage may include a frame having wheels thereon which can track along rails formed on the upper side of the treatment chamber. Preferably, the distributor conveyor extends the full width of the treatment chamber and in one form is disposed below the side walls thereof in order to prevent spillages. The moving portion of the distributor belt may be adapted to travel across and is supported by the stationary portion of the belt.

The feed system may further include a feed hopper which receives material from the pretreatment system. The feed hopper may be arranged so as to feed material therein onto a delivery conveyor driven manually or by a motor. The feed hopper may be disposed at an upstream end of the delivery conveyor. Downstream of the feed hopper there may be provided a leveling device which controls the depth of material on the delivery conveyor. The leveling device may include an endless belt, chains or other flexible element. The flexible elements may be adapted to rotate in a direction against the direction of travel of the delivery conveyor having paddles thereon. Downstream of the leveling device a ruffler assembly may be provided which includes a shaft or drum upon which a plurality of tines are mounted. The purpose of the ruffler assembly is to loosen the material prior to it leaving the delivery conveyor.

Drive means in the form of a motor and flexible line may be provided for moving the carriage. The drive means may include a winch for pulling the carriage across the top of the treatment chamber. The winch need not be powered but may be manually operable. In another arrangement the carriage may be self powered by a motor thereon for driving one or more of the carriage wheels.

The distributor conveyor and delivery conveyor may be arranged to travel at selected different speeds so as to provide for a dynamic control of the depth of material on the distributor conveyor.

A rake unit may be provided on the carriage to aerate the material.

According to yet another aspect of the present invention there is provided a harvester which is suitable for use with apparatus of the type described above, the harvester including a main frame operatively mounted for movement relative to the main body of the treatment apparatus in a position below the base thereof. The harvester further includes tool carried by the frame for extracting material from the treatment chamber. The tool may be of the type described in the earlier mentioned patent specification WO 99/51545.

In one form the frame includes wheels which are adapted to run on rails mounted to the main body of the treatment apparatus. The frame may be suspended from rails disposed adjacent the base of the treatment apparatus or supported on rails spaced from the main body of the treatment apparatus. Drive means may be provided for causing movement of the main frame along the rails. The drive means may be of the same type described earlier for driving the carriage of distributor assembly of the feed system. The tool may be adapted to rotate at different selected speeds to optimize extraction of material from the treatment chamber. Furthermore, the harvester may be adjustable so that the tool can enter the treatment chamber through the base to a selected depth. In one form the tool is mounted to the main frame through an over centre linkage which permits movement of the tool relative to the frame.

Preferred embodiments of the invention will be hereinbefore described with reference to the accompanying drawings, and in those drawings.

Figure 1:
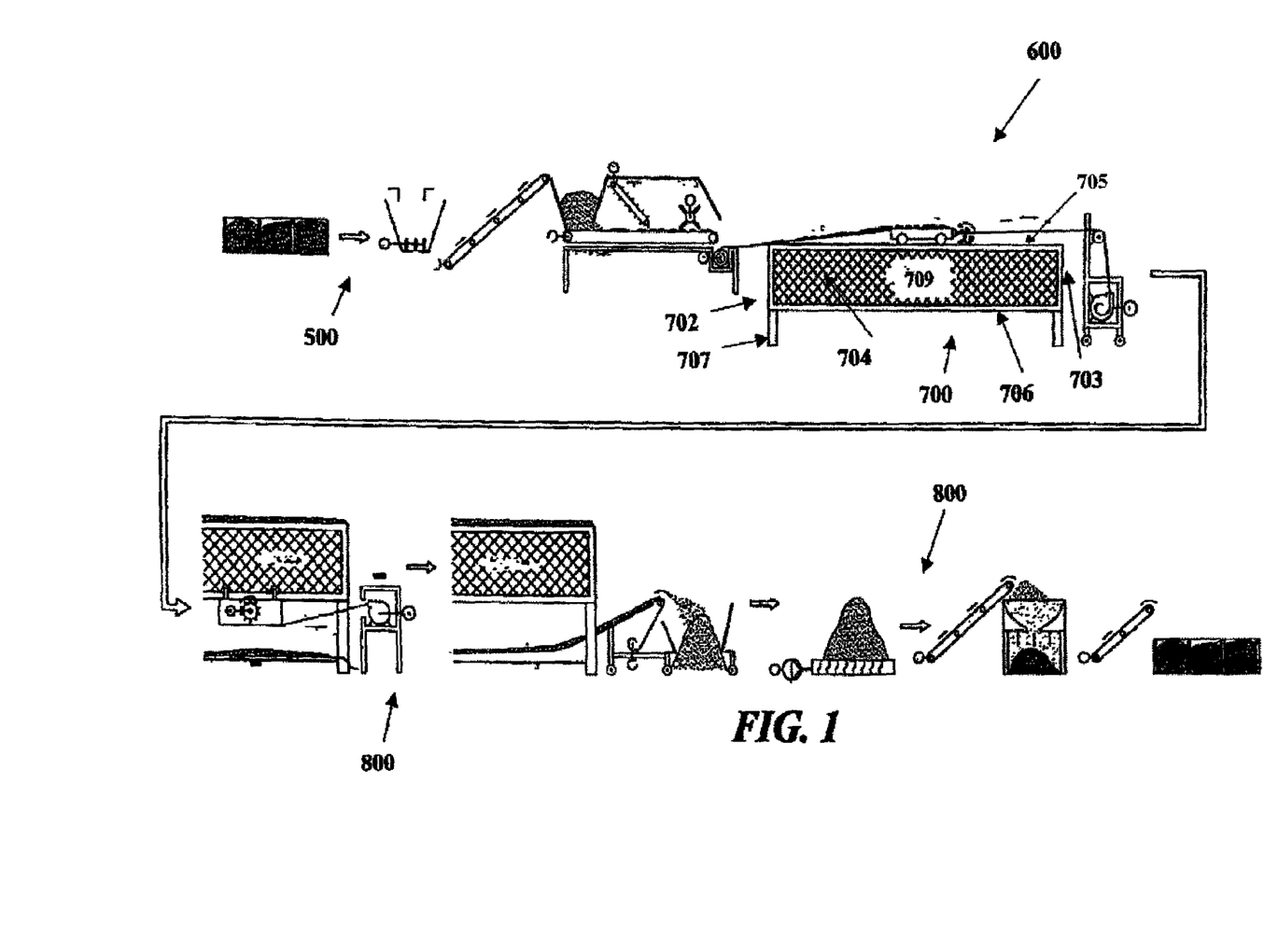
FIG. 1 is a schematic side view of apparatus for use in vermiculture processing systems.

The apparatus shown in FIG. 1 includes a pretreatment system 500, a feed system 600, a treatment system 700, and a harvester and collecting assembly 800.

The treatment system 700 includes a treatment bed or receptacle 702 which may be of the type described in International Patent Specification No. WO 99/51545 (PCT/AU99/00238). The apparatus 702 includes a main body 703 having a peripheral side wall 704 with an upper edge 705 and a lower edge 706. A treatment chamber 709 is disposed within the apparatus 702, the apparatus having an open top and a base which includes a plurality of support elements which are spaced apart sufficiently to support material to be treated within the chamber and enable extraction of the treated material by a harvester. The main body 703 is supported on legs 707 so that there is a space below the treatment chamber for harvesting and collection of the treated material. This structure is described in detail in the aforementioned International patent specification.

Figure 2:
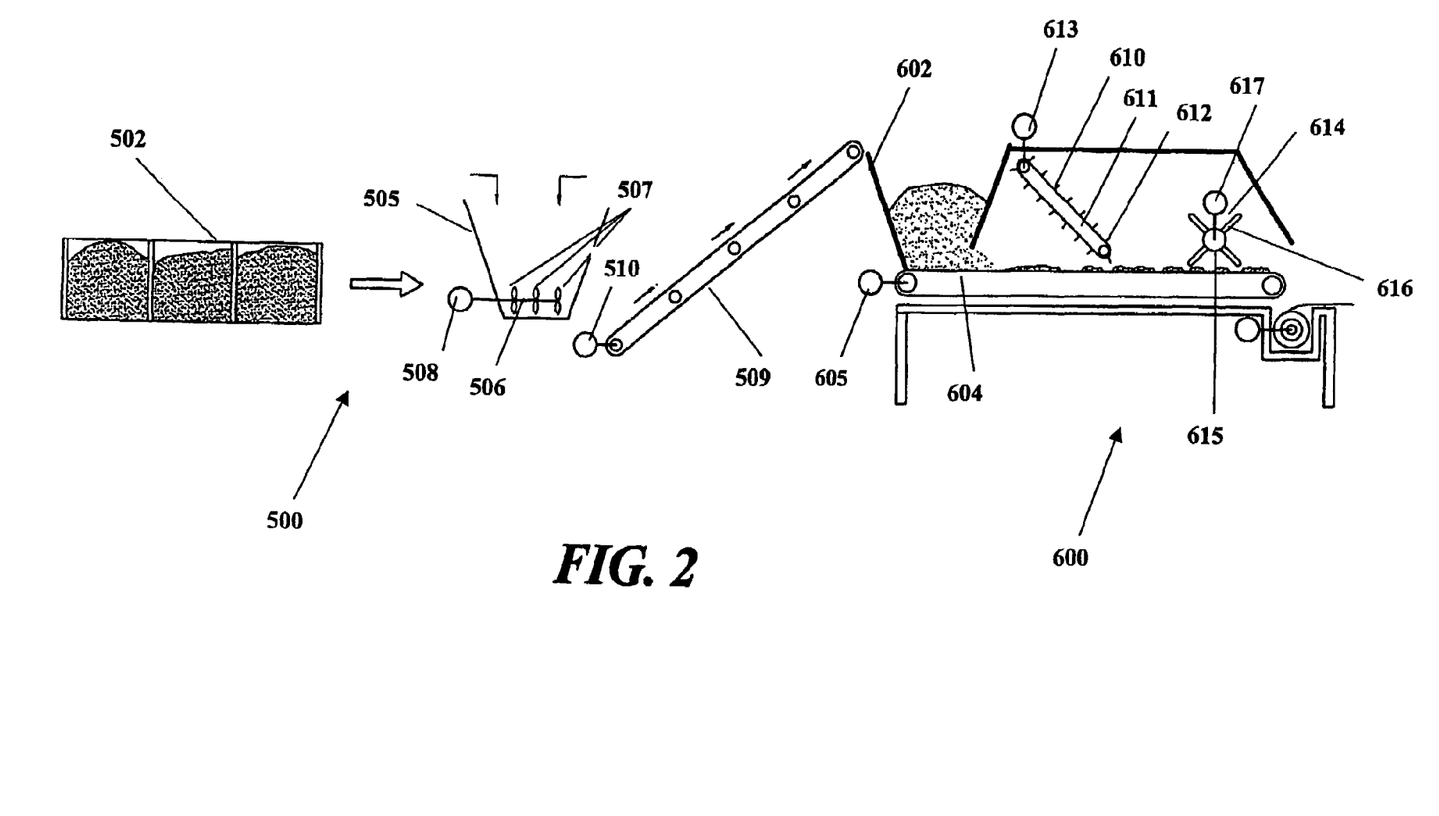
FIG. 2 is a more detailed schematic view of a pretreatment and part of a feed system which forms part of the apparatus shown in FIG. 1.
Figure 3:
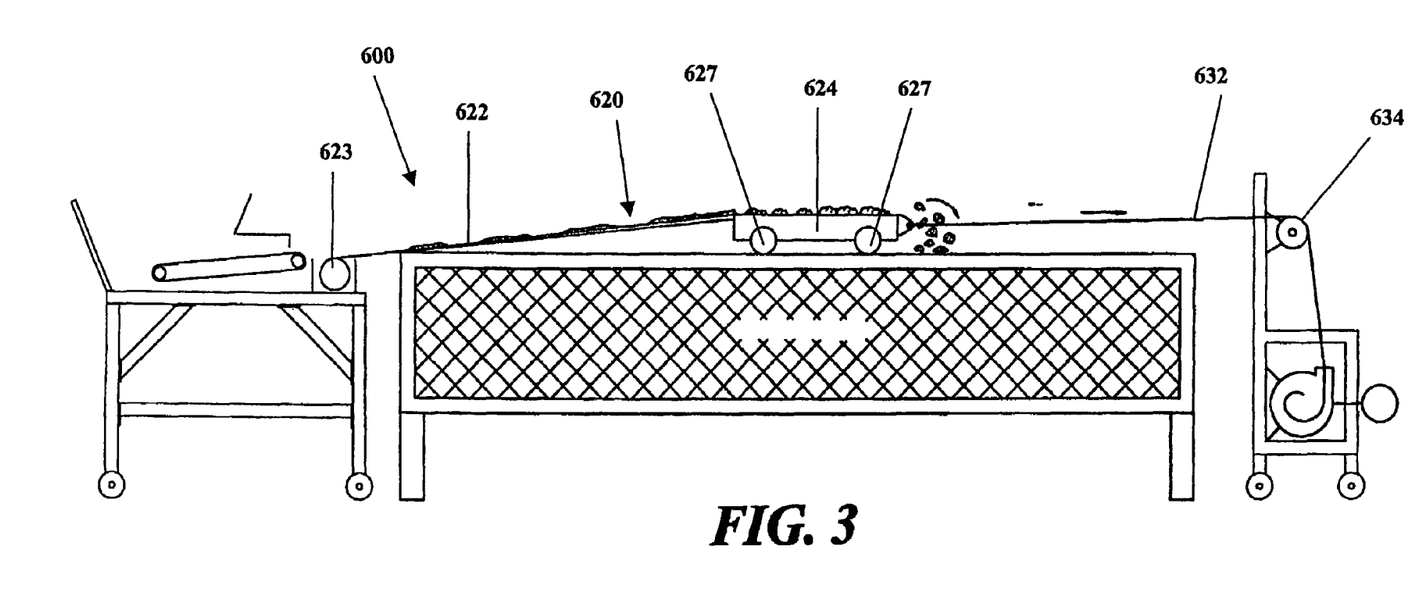
FIG. 3 is a more detailed schematic view of part of a feed system which forms part of the apparatus shown in FIG. 1.

Referring in particular to FIG. 2 the pretreatment system 500 includes a mixing vessel 505 to which unprocessed waste material is delivered from storage bunkers 502. The mixing vessel 505 includes a mixer 506 in the form of rotating paddles, ribbons or tynes 507 driven by a motor 508 which mixes the material within the vessel. One or more additives may be supplied to the material within the mixing vessel. The material within the vessel is transferred to the feed system 600 via transfer conveyor 509 driven by a motor 510.

Referring in particular to FIGS. 3, 4 and 10 to 15 the feed system 600 includes a feed hopper 602 which receives material from the transfer conveyor 509. The feed hopper 602 is arranged so as to feed material therein onto a delivery conveyor 604 driven by a motor 605. The feed hopper 602 is disposed at an upstream end of the delivery conveyor 604. The feed hopper 602 may include skirts 603 (FIG. 10) extending downwardly therefrom so as to be adjacent the conveyor 604 so as to assist in retaining the material on the conveyor. The hopper may further have a rear door (not shown) through which material can be discharged prior to travelling along the conveyor. Downstream of the feed hopper 602 there is provided a leveling device 610 which controls the depth of material on the delivery conveyor 604. The leveling device 610 includes an endless belt 611 driven by motor 613 having paddles 612 thereon. Downstream of the leveling device 610 is a ruffler assembly 614 which includes a rotatable shaft or drum 615 driven by motor 617 and upon which a plurality of tines 616 are mounted. The purpose of the ruffler assembly is to prepare the material prior to it leaving the delivery conveyor by for example, breaking up any residual clumps and/or aerating the material.

Figure 4:
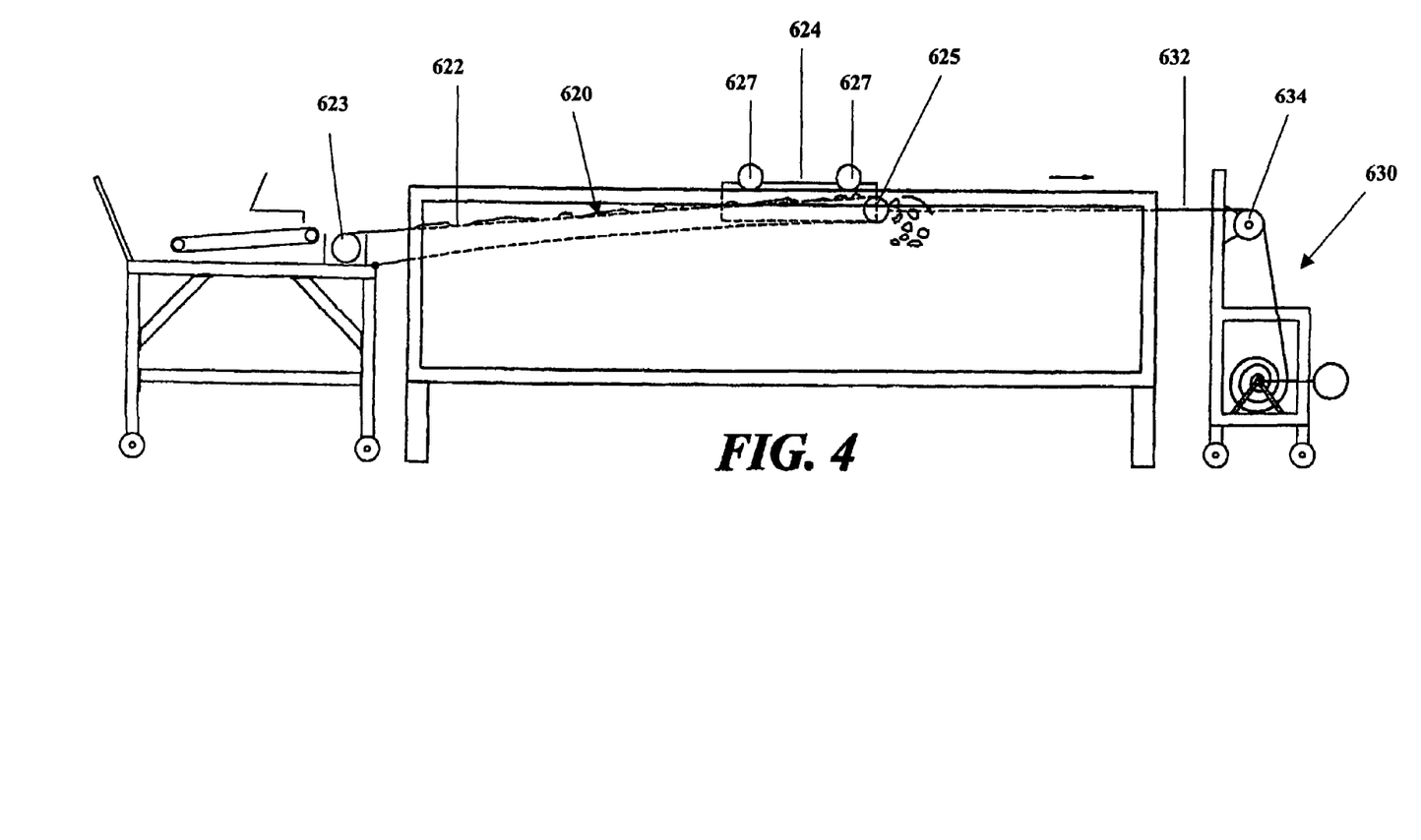
FIG. 4 is a slightly modified form of that part of the apparatus shown in FIG. 3.

The feed system 600 further includes a material distributor assembly 620 for distributing the material into the treatment chamber. The distributor assembly 620 includes a distributor conveyor 622 which is adapted to be wound around onto or from a conveyor drum 623. The assembly further includes a carriage 624 which is adapted to traverse over the top of the treatment chamber. The carriage includes an idler roller 625 thereon (FIG. 4) over which the distributor conveyor passes with its free end being anchored to a fixed structure. Thus as the carriage moves over the treatment chamber the conveyor is drawn from the drum and passes around the idler drum so that material on the conveyor is evenly distributed into the treatment chamber. The carriage 624 includes a frame having wheels 627 thereon which can track along rails formed on the upper side of the treatment chamber. The distributor conveyor extends the full width of the treatment chamber and as shown in the embodiment of FIG. 4 is disposed below the side walls thereof in order to prevent spillages. The moving portion of the distributor belt (that is the upper portion) travels across and is supported by the stationary portion of the belt.

Drive means 630 in the form of a motor 631 and flexible line 632 may be provided for moving the carriages. The drive means may include a winch 634.

The distributor conveyor and delivery conveyor may be arranged to travel at selected different speeds so as to provide for a dynamic control of the depth of material on the distributor conveyor. A rake unit 637 (FIG. 18) may be provided on the carriage to aerate the material.

The harvester 810 includes a frame 811 mounted to the treatment chamber bed for movement below the base thereof. The harvester may include a tool of the type described in the earlier mentioned patent specification WO 99/51545.

Figure 5:
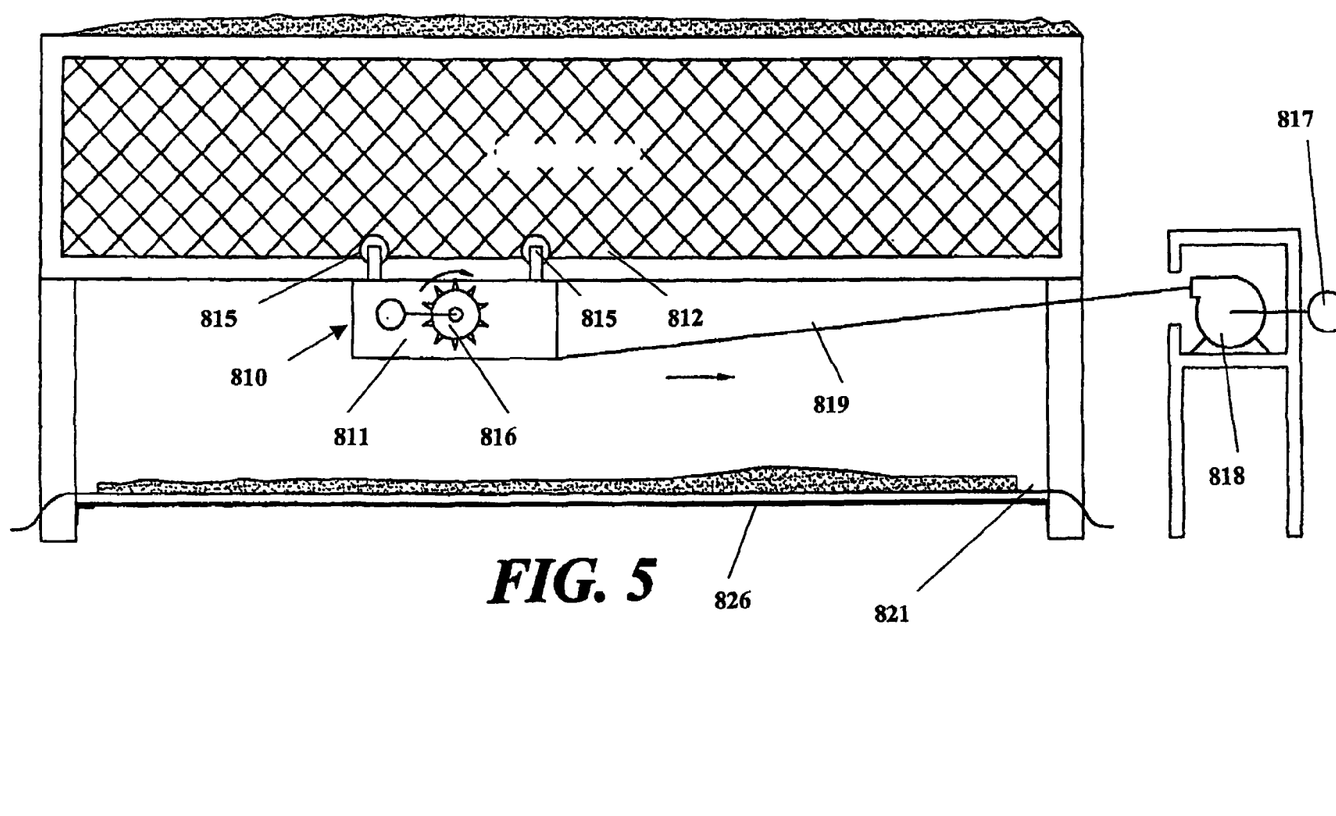
FIG. 5 is a more detailed schematic view of a harvesting apparatus and collecting system which forms part of the apparatus shown in FIG. 1.
Figure 16:
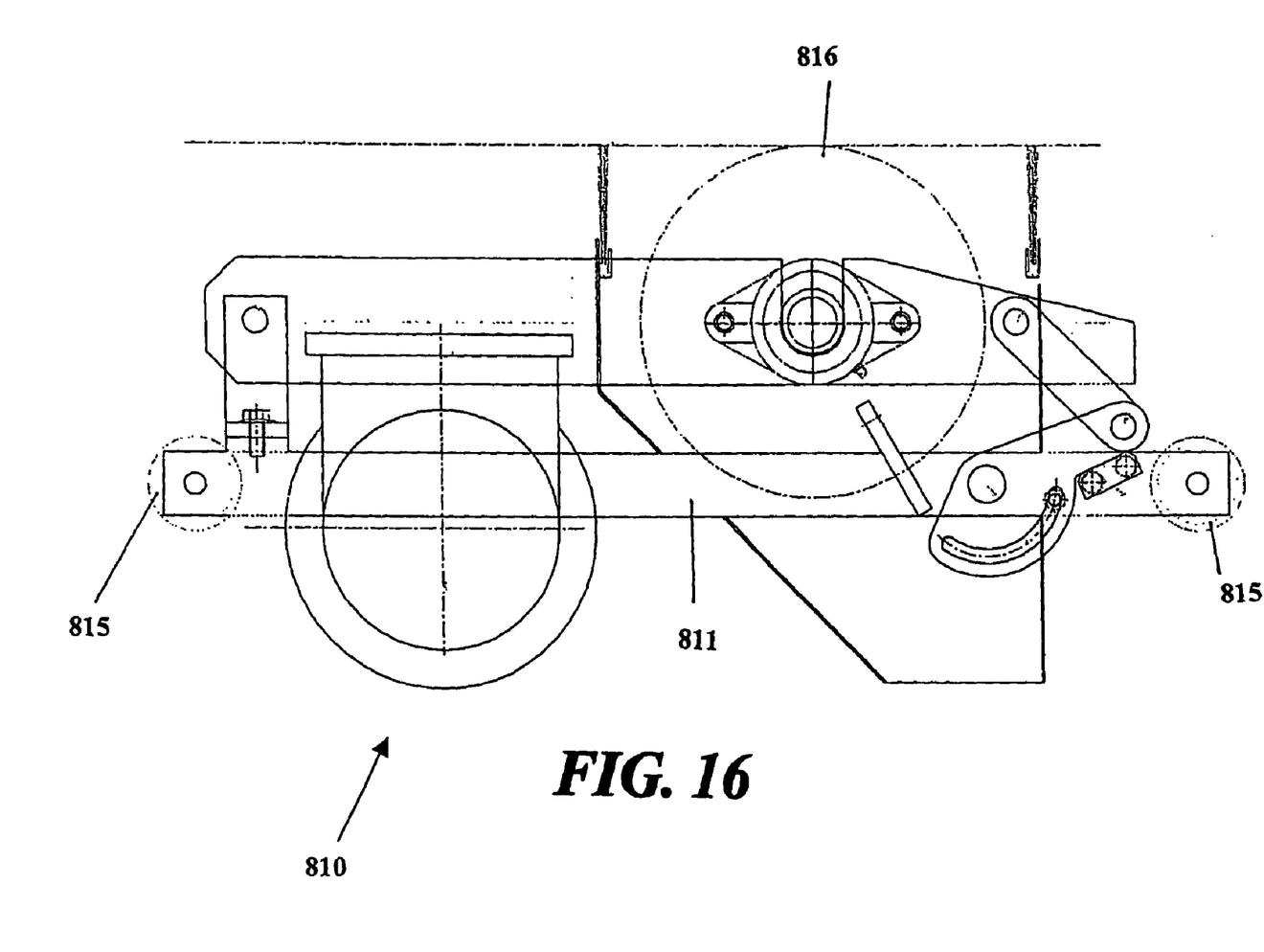
FIGS. 16 and 17 are more detailed schematic views of a harvester according to the invention.
Figure 17:
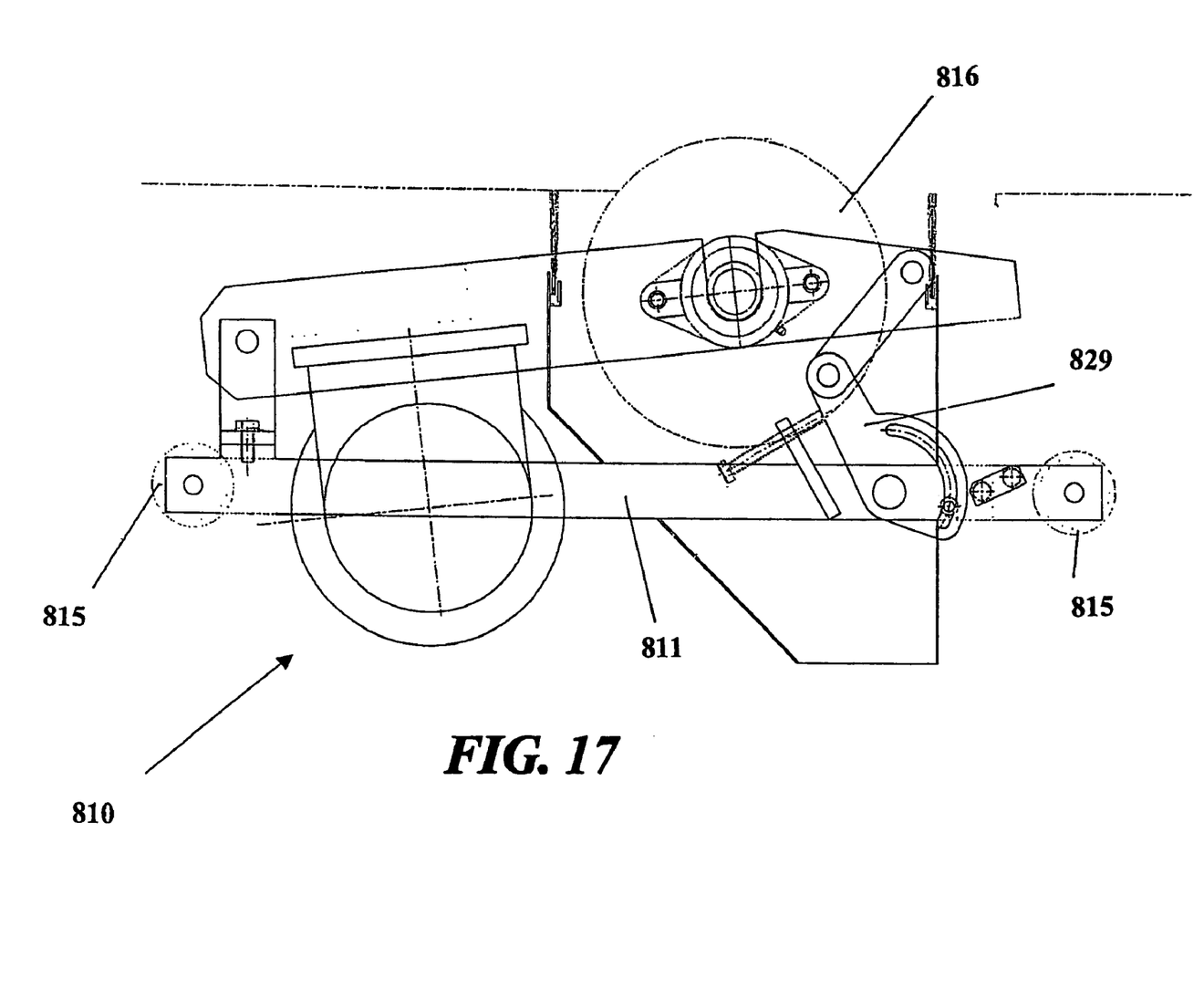

Referring to FIGS. 5, 16 and 17 there is shown a harvester 810 which includes a main frame 811 operatively mounted for movement relative to the main body 703 of the treatment apparatus 702 in a position below the base thereof The harvester further includes tool 816 carried by the frame 811 for extracting material from the treatment chamber. The tool may be of the type described in the earlier mentioned patent specification WO 99/51545.

In one form the frame 811 includes wheels 815 which are adapted to run on rails 812 mounted to main body of the treatment apparatus. The frame may be suspended from rails disposed adjacent the base of the treatment apparatus or supported on rails spaced from the main body of the treatment apparatus. Drive means may be provided for causing movement of the main frame along the rails. The drive means may be of the same type described earlier for driving the carriage of distributor assembly of the feed system; that is, the drive means may comprise a motor 817, a winch 818 and a tow line 819 (FIG. 5). The tool 816 may be adapted to rotate at different selected speeds to optimize extraction of material from the treatment chamber. Furthermore, the harvester may be adjustable so that the tool can enter the treatment chamber through the base to a selected depth. As shown in FIGS. 16 and 17 the tool 816 is mounted to the main frame through an over centre linkage 829 which permits movement of the tool relative to the frame.

Figure 6:
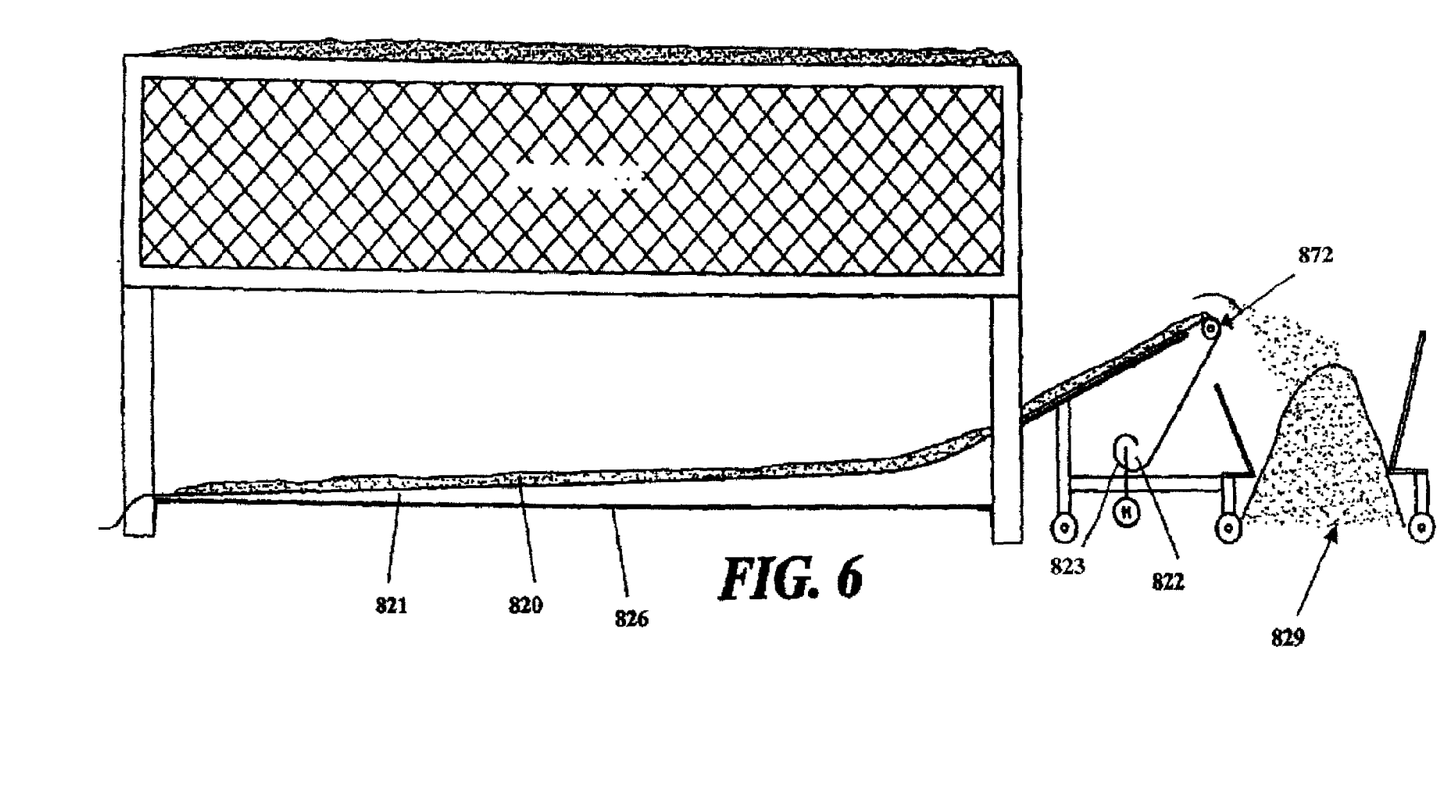
FIG. 6 is a more detailed schematic view of a collecting system which forms part of the apparatus shown in FIG. 1.
Figure 7:
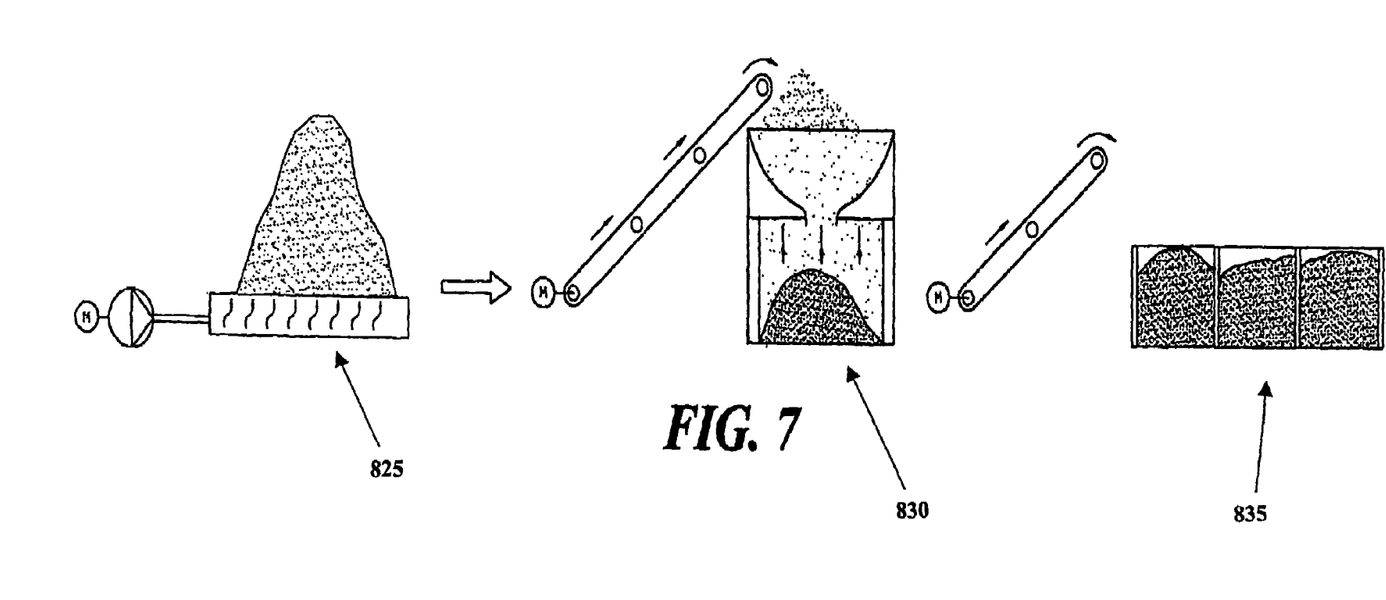
FIG. 7 is a more detailed schematic view of a collecting system which forms part of the apparatus shown in FIG. 1.
Figure 8:
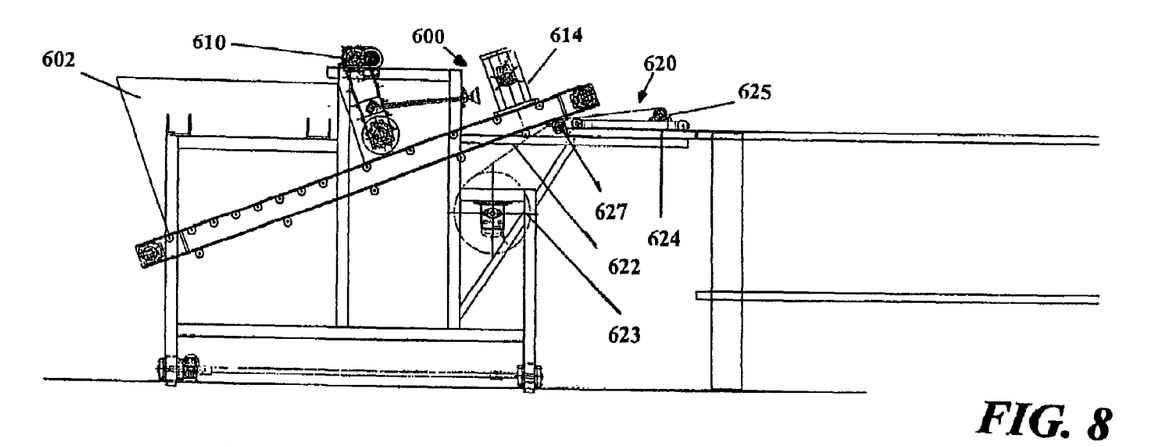
FIGS. 8 and 9 are schematic side views of a modified form of feed system according to the invention.
Figure 9:
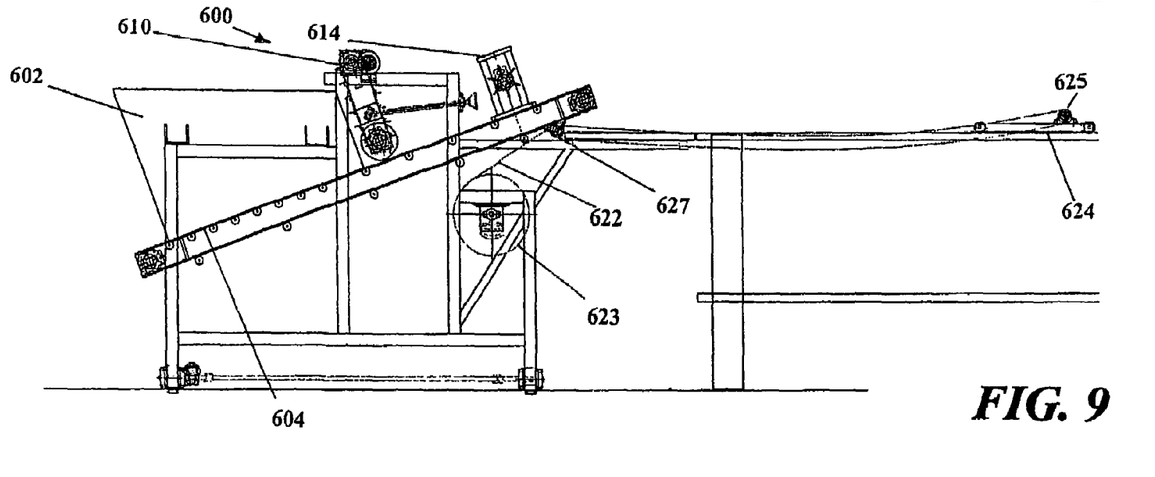
Figure 10:
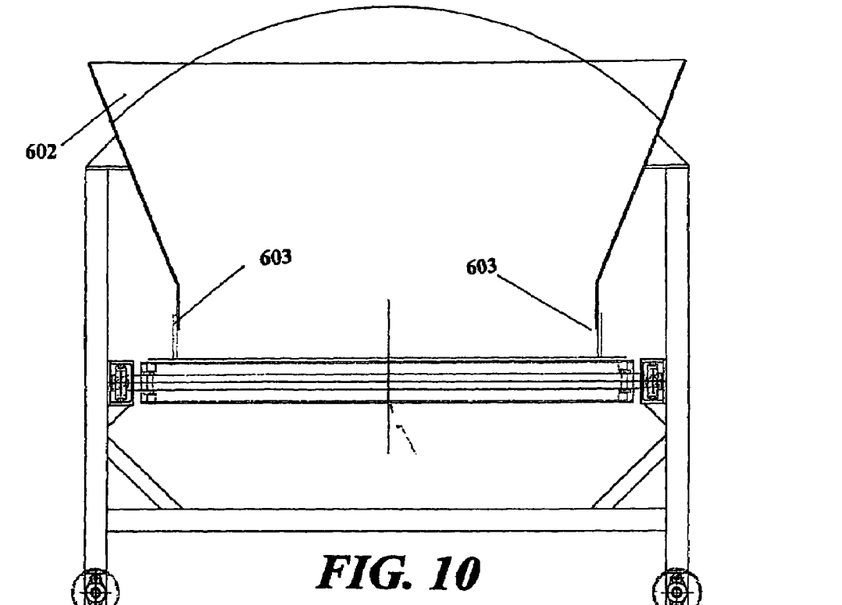
FIG. 10 is an end view of the feed system shown in FIGS. 8 and 9.
Figure 11:
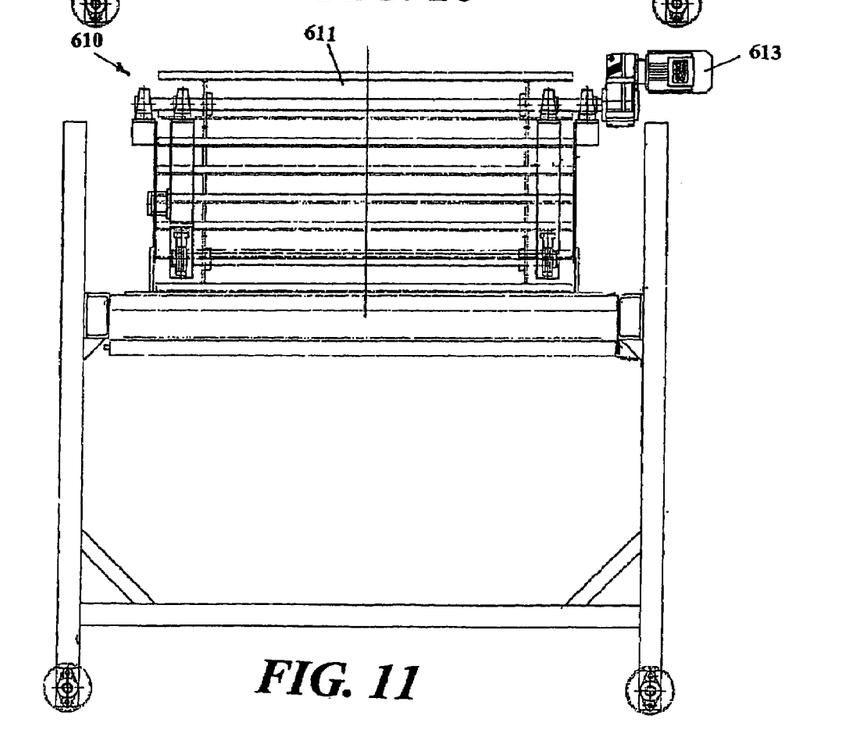
FIG. 11 is a more detail view of part of the feed system shown in FIGS. 8 and 9.
Figures 12, 13:
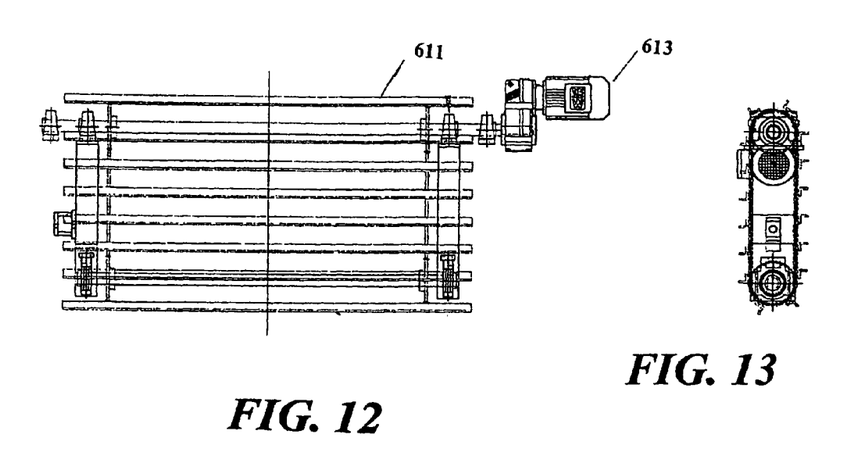
FIG. 12 is a side view of a leveling device forming part of the feed system shown in FIGS. 8 and 9.
FIG. 13 is an end view of the device shown in FIG. 12.
Figures 14, 15:
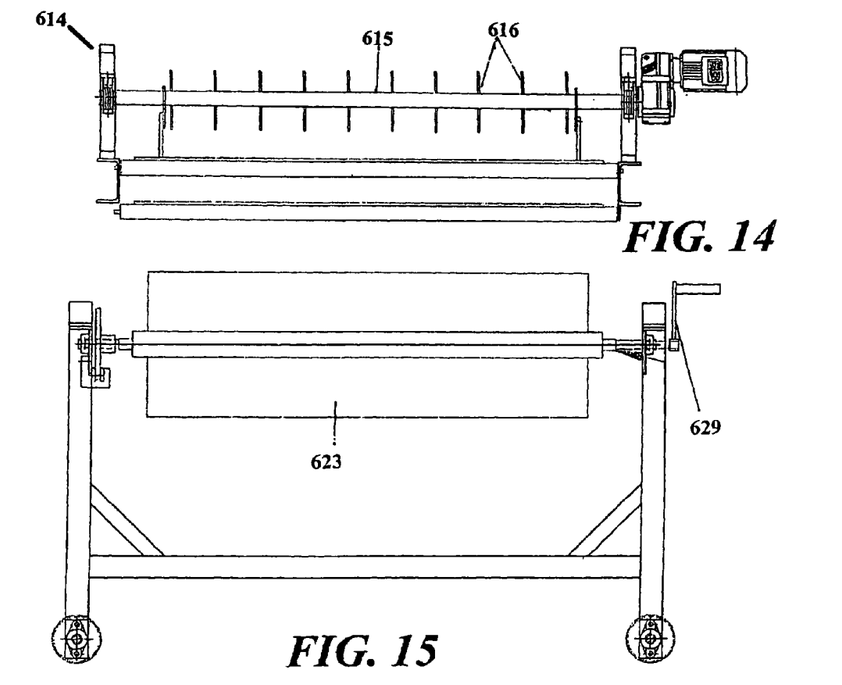
FIG. 14 is an end view of a ruffler which forms part of the system shown in FIGS. 8 and 9.
FIG. 15 is an end view of part of the system shown in FIGS. 8 and 9.

The collecting assembly 800 as best seen in FIG. 6 includes a flexible belt conveyor 821 which is adapted to be wound on and retracted from a rotatable member 822 in the form of a winch drum 823. When retracted, the belt adopts a collecting position under the receptacle 702 so that harvested material can fall onto the belt. In the collecting position the belt is supported on a tray 826. The tray 826 may include a base and side walls for assisting in retaining the harvested material on the belt.

In the particular form shown in FIG. 6 the belt 821 passes over a pulley or roller 872 before being wound onto the winch drum 823. As the belt is wound onto the winch drum material is discharged into a collecting region 829. The belt can be retracted from the drum by a simple manual operation or may be pulled therefrom using any suitable device. Material is transferred to a drying chamber 825 after which is transferred to a screening device 830. The finally treated material is transferred to storage or dispatch bunkers 835.

FIGS. 8 to 15 illustrate a modified form of feed system to that shown in the earlier drawings. Like reference numerals have been used to identify the like parts described in the earlier drawings. In this embodiment the delivery conveyor 604 is inclined. The distributor conveyor 622 passes over a roller 627 and then extends around idler roller 625 on carriage 624 and is anchored at a fixed point on a frame which carries the delivery conveyor. The conveyor drum 623 has a handle 629 mounted thereto for manually returning the carriage to the position shown in FIG. 8.

Figure 18:
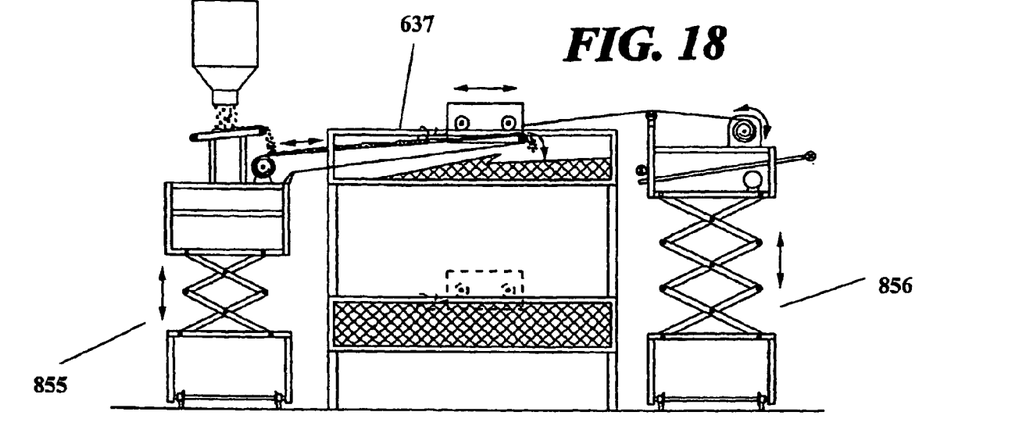
FIGS. 18 to 20 are schematic side elevations of further modified forms of the invention.
Figure 19:
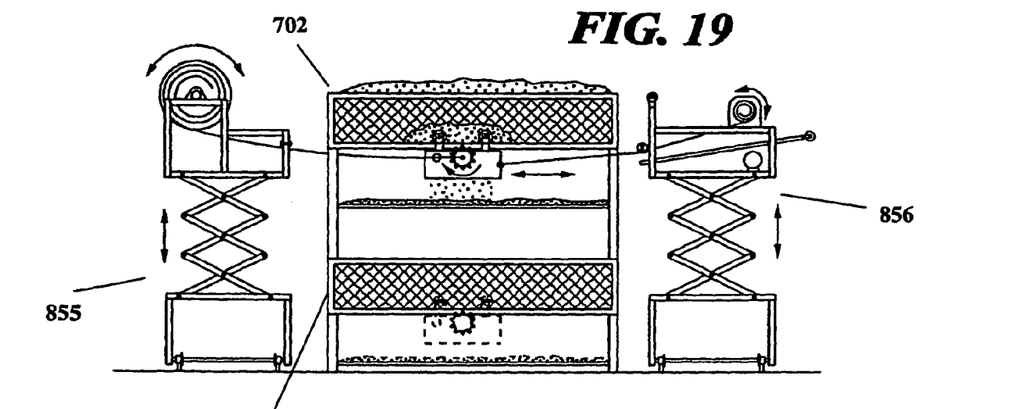
Figure 20:
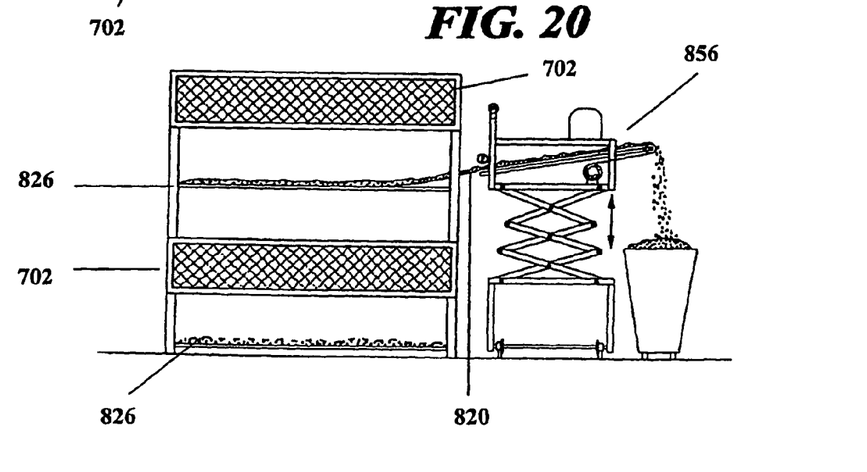

Referring to FIGS. 18 to 20 there is shown a multiple tiered form of apparatus. In the form shown a series of receptacles 702 are mounted one on top of the other. The drawings illustrate a two tiered arrangement however it would be appreciated that three or more tiers could be provided. Each tier includes a tray 826 for supporting the collecting belt 820 thereon. Further each receptacle has a rail system thereon for carrying the harvester and a further rail system for supporting the feeder.

In the form shown a single feeder, harvester and collection belt are provided, each of these devices have been movable between one receptacle and the other by means of lifting mechanisms 855 and 856. A single rotatable winch drum may be used for driving each of the feeder mechanism, harvester and collection belt. The above arrangement has the advantage that heavy moving loads are significantly reduced; that is, the feed belt and collection belt distribute the load evenly across the bed and hence enable is light weight bed design. It will be appreciated that harvesting and feeding could occur at the same time.

Other arrangements and advantages of the present invention will hereinafter be described.

In one arrangement one of the collection belts can be left beneath each receptacle so that each belt can capture harvest drips and prevent them falling on the floor or onto bed below in the case of tiered systems. The receptacles can be very long, and the quantity of harvest collected can be great. If using a collecting hopper, the moving loads being transported would be significant and would require substantial receptacle structures to carry the weight The present invention allows the weight to be distributed evenly across the whole surface area, reducing the weight and strength required of the or each receptacle. Alternatively, the collecting hopper would have to make numerous trips back and forth to discharge collected material. Such trips would be inefficient and the present invention allows material to be collected in one go. The present invention allows material to receive some air drying where on the collection belt and allows subsequent dripping of harvest to be collected Because it allows an interval between harvest and collection this improves operational efficiency. The above is all true of the feeder arrangement described earlier as well. Furthermore, having one harvester as in one preferred form allows it to be transported from receptacle to receptacle and thus saving equipment.

The collection belt can be formed of woven netting material so as to be lightweight and strong. It will be appreciated that other material could be used. Furthermore, it can be of a smooth finish to minimize abrasion and wear and reduce friction when pulling and can be arranged so that it is pulled out or pulled back using hand force (hand-winder winch or even rope or the like) or mechanical drive such as a motor. The tray and belt may be arranged so that the feeding of the receptacle below can be conducted without interfering with, or necessitating the removal of the tray; that is there is sufficient space provided for feeding the receptacle below with the tray/belt still in place. On the lower most tier, the support tray can be a mesh to allow cleaning of the floor area if the belt is removed Finally, it is to be understood that various alterations, modifications and/or additions may be incorporated into the various constructions and arrangements of parts without departing from the spirit or ambit of the invention.

We claim:

1. Apparatus for use in a vermiculture plant, the apparatus including a treatment receptacle having a treatment chamber therein and a base upon which material within the treatment chamber is disposed, the receptacle being arranged so that when in use there is a space below the base, a harvester operable to extract material from the treatment chamber through the base and a collecting assembly including a flexible belt operatively connected to a rotatable drum so that it can be wound onto or drawn from the rotatable member, said belt being arranged so that it can adopt a collecting position when at least partially unwound from the rotatable member wherein it is positioned below the treatment chamber and harvester so that harvested material can be collected upon it, said belt being operable so that when the belt is wound onto the rotatable member material thereon can be transferred to a discharge zone, the apparatus further including a feed system, the feed system including a material distributor assembly for distributing the material into the treatment chamber, the distributor assembly including a distributor conveyor which is adapted to be wound onto or from a rotatable member, the assembly further including a carriage which is adapted to traverse over the top of the treatment chamber, the carriage including an idler roller thereon over which the distributor conveyor passes with its free end being anchored to a fixed structure.

2. Apparatus according to claim 1 wherein said rotatable member is a rotatable drum arranged so that the belt can be wound around the drum and retracted from underneath the treatment chamber.

3. Apparatus according to claim 2 wherein the discharge zone is disposed adjacent the drum so that as the belt is wound onto the drum material is discharged from the belt.

4. Apparatus according to claim 1 wherein said collecting assembly further includes a support tray upon which the belt rests when in the collecting position.

5. Apparatus according to claim 4 wherein said support tray includes side walls between which the belt is disposed.

6. Apparatus according to claim 1 wherein said belt is porous.

7. Apparatus according to claim 1 wherein the harvester includes a main frame operatively mounted for movement relative to the main body of the treatment apparatus in a position below the base thereof, the harvester further including tool carried by the frame for extracting material from the treatment chamber.

8. Apparatus according to claim 7 wherein the harvester body is suspended from rails disposed adjacent the base of the treatment apparatus or supported on rails spaced from the main body of the treatment apparatus, and includes drive means for causing movement of the main frame along the rails.

9. Apparatus according to claim 8 wherein the belt is retractable generally in the same direction of movement of the harvester.

10. Apparatus according to claim 1 wherein there is provided a plurality of said treatment receptacles disposed one above the other in a tiered configuration.

11. Apparatus according to claim 10 wherein each said treatment receptacle has associated therewith one said harvester and one said collecting assembly.

12. Apparatus according to claim 10 wherein said harvester is adapted to be moved into a harvesting position for each treatment receptacle and said flexible belt of said collecting assembly is adapted to be positioned for use with each treatment receptacle.

13. Apparatus according to claim 12 further including a lifting mechanism for transferring said harvester and said flexible belt of said collecting assembly between said treatment receptacles.

14. Apparatus according to claim 12 wherein a single said rotatable member can be used for moving said harvester and said flexible belt of said collecting assembly.

* * * * *